United States Patent

Robertson

[11] Patent Number: 6,153,104
[45] Date of Patent: *Nov. 28, 2000

[54] BODY FLUID SEPARATION MEANS

[75] Inventor: Patricia Mary Beckett Robertson, Appleby in Westmorland, United Kingdom

[73] Assignee: Phoenix Medical Limited, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,942
[22] PCT Filed: Nov. 6, 1995
[86] PCT No.: PCT/GB95/02599
 § 371 Date: Oct. 21, 1997
 § 102(e) Date: Oct. 21, 1997
[87] PCT Pub. No.: WO96/14578
 PCT Pub. Date: May 17, 1996

[30] Foreign Application Priority Data

Nov. 8, 1994 [GB] United Kingdom .................. 9422504

[51] Int. Cl.⁷ .................................................. B01D 29/00
[52] U.S. Cl. ..................... 210/650; 210/406; 210/416.1; 210/433.1; 210/435; 422/101; 436/177
[58] Field of Search .................................. 210/645, 650, 210/651, 767, 258, 406, 416.1, 433.1, 435; 422/101, 102; 436/177, 178; 435/2

[56] References Cited

U.S. PATENT DOCUMENTS

| 3,567,029 | 3/1971 | Quame .................................... 210/249 |
| 4,304,865 | 12/1981 | O'Brien et al. ......................... 422/101 |
| 4,357,240 | 11/1982 | Mehra et al. ............................ 210/472 |
| 4,787,988 | 11/1988 | Bertoncini et al. ..................... 210/406 |
| 4,966,758 | 10/1990 | Belt ......................................... 422/101 |
| 5,164,087 | 11/1992 | Naoi et al. ......................... 210/500.21 |
| 5,240,862 | 8/1993 | Koenhen et al. .................. 210/500.24 |
| 5,306,420 | 4/1994 | Bisconte .................................. 210/541 |
| 5,364,533 | 11/1994 | Ogura et al. ............................ 210/504 |
| 5,380,437 | 1/1995 | Bertoncini ............................ 210/416.1 |
| 5,380,483 | 1/1995 | Sklar et al. .............................. 210/232 |
| 5,447,842 | 9/1995 | Simons ...................................... 435/6 |
| 5,457,024 | 10/1995 | Goldbard .................................... 435/2 |
| 5,490,927 | 2/1996 | Herczeg ............................. 210/321.84 |
| 5,501,954 | 3/1996 | Mahr et al. ................................ 435/6 |
| 5,603,900 | 2/1997 | Clark et al. ............................. 422/101 |
| 5,624,815 | 4/1997 | Grant et al. ............................ 210/405 |
| 5,647,985 | 7/1997 | Ung-Chhun et al. .................. 210/504 |
| 5,665,238 | 9/1997 | Whitson et al. ....................... 210/504 |
| 5,707,526 | 1/1998 | Kraus et al. ........................... 210/504 |
| 5,728,267 | 3/1998 | Flaherty ............................. 210/321.67 |

FOREIGN PATENT DOCUMENTS

| 8904501 | 11/1989 | Germany . |
| 2232599 | 12/1990 | United Kingdom . |
| WO 92/18844 | 10/1992 | WIPO . |
| WO92/17110 | 10/1992 | WIPO . |
| WO94/17209 | 8/1994 | WIPO . |

*Primary Examiner*—John Kim
*Attorney, Agent, or Firm*—Trexler, Bushnell, Giangiorgi & Blackstone, Ltd.

[57] ABSTRACT

A body fluid separation device which includes at least one first chamber, a cooperating filter extending across the or each first chamber and at least one second chamber respectively to cooperate with the at least one first chamber characterized in that one or both of the first and second chambers has a connection to vacuum, positioned to one or both sides of the filter and there being a removable closure in the form of end caps at the end of each chamber, wherein the body fluid separation device is disposable.

6 Claims, 2 Drawing Sheets

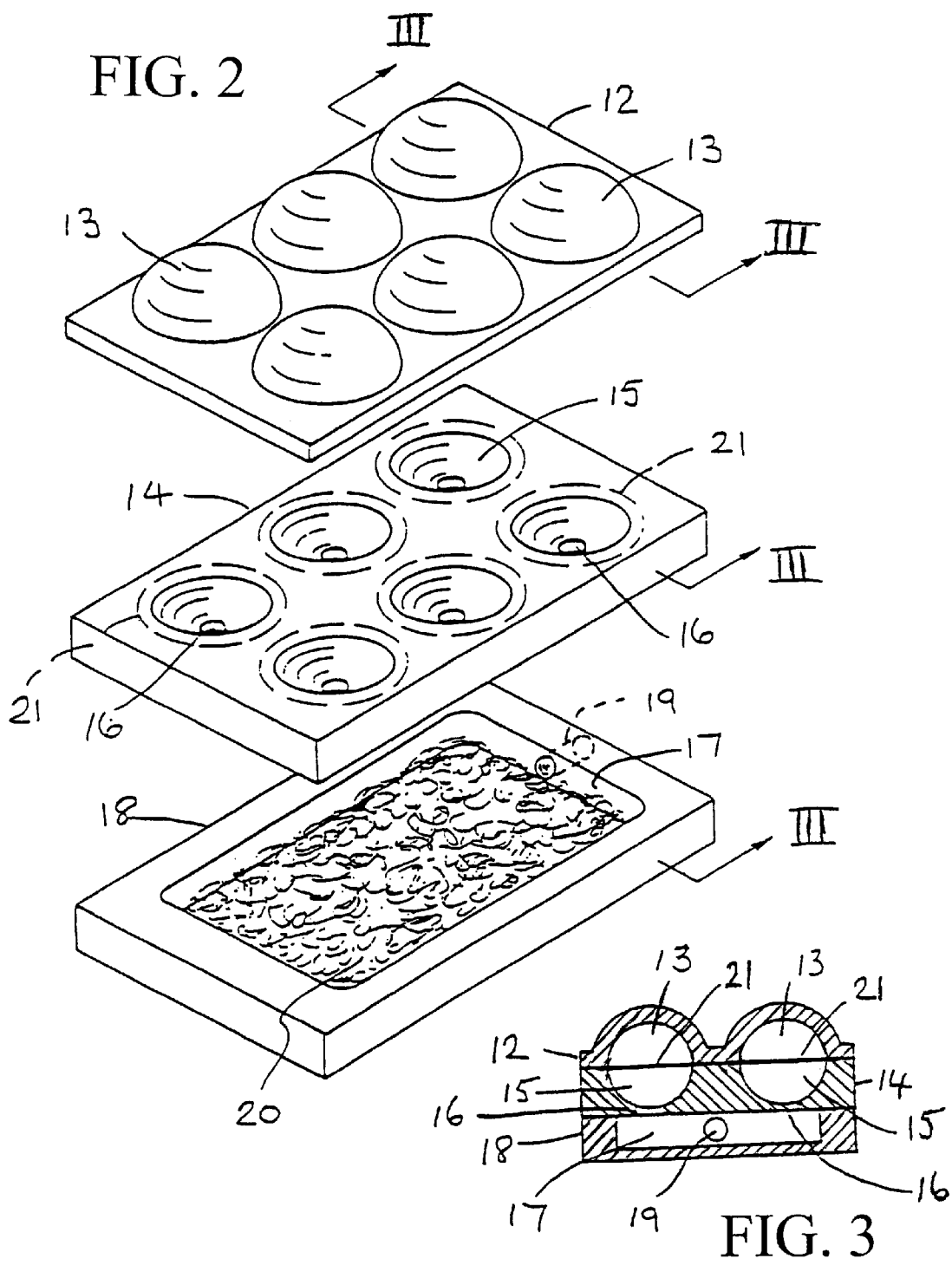

BODY FLUID SEPARATION MEANS

CROSS-REFERENCE

This application is a 371 of PCT/GB95/02599 which was filed on Nov. 6, 1995 claiming the priority of British patent application no. 9422504.2, which was filed on Nov. 8, 1994.

BACKGROUND

This invention relates to body fluid testing, and is particularly concerned with the separation of blood into various of its components, to enable a variety of tests to be performed, and to the separation of other body fluids, such as, bone marrow, sperm/seminal plasma, urine, and saliva.

In the field of hematology and related areas such as gene therapy and forensic pathology, and in other fields, such as the determination of sperm fertilising potential and cell separation from bone marrow, hitherto it has involved complex and expensive apparatus and procedures, and has required considerable operator skills to separate correctly the components of the paticular body fluid. This has been particularly so with blood, consequent on the need for careful preparation of a blood sample.

In other areas such as the testing or screening of a foetus for one or more of a number of possible abnormalities, it has hitherto predominantly been effected by invasive techniques frequently to the discomfort of the mother.

SUMMARY

It is the object of the invention to provide equipment of notable simplicity and relatively low cost, with attendant procedures well within the capabilities of junior members of laboratory staff, to enable separation of a body fluid into various of its components.

According to a first aspect of the present invention, a body fluid separation means comprises at least one first chamber, a cooperating filter extending across the or each first chamber, at least one second chamber respectively to cooperate with the at least one first chamber, and one or both of said first and second chambers having a connection to vacuum.

According to a second aspect of the invention, a body fluid separation means comprises a chamber, a filter extending across the chamber, a removable closure means at each end of the chamber and a connection means to connect the chamber to vacuum positioned to one or both sides of the filter.

According to a third aspect of the invention, a body fluid separation means comprises a first plate formed with two or more collection chambers, a second plate with a corresponding number of waste receiving chambers, a connection to vacuum for each said waste receiving chamber, a filter means between each collection chamber and cooperating waste receiving chamber, and a third plate forming a vacuum chamber to connect each waste receiving chamber to vacuum.

With the second aspect of the invention, the removable closure means may simply be a cap fitted to and in sealing engagement with the end of the chamber, and a second cap may be provided to be fitted to the opposite end of the chamber.

With the third aspect of the invention, the first plate, second plate, and third plate, are preferably detachably secured in sealing engagement, with the filters trapped between the first and second plates.

Insofar as each usage of the invention in any of its aspects is concerned, the filter extending across one end of the chamber, bridging a chamber, or trapped between the first and second plates is selected to suit the body fluid to be tested, and if required, is pre-treated in a manner making it suitable for use with the body fluid to be tested. Thus, in one form of construction it is preferred that a leukocyte trapping membrane filter is provided. Where it is a case of the separation of cells, a replaceable filter is provided of a character that permits the passage of, for example, maternal blood cells and the entrapment of, for example, foetal blood cells. In the case of sperm testing, the filter will enable the passage of seminal fluid whilst trapping the sperm. Similarly with bone marrow, the filter is selected to suit the entrapment of bone marrow cells whilst allowing the passage of plasma.

The material of the chamber and of the or each end cap, and the material of each plate, may be such that the chamber and the cap(s) and the plates, can be sterilised, such as by, for example, gamma radiation. The filter is preferably a disposable component, formed from a relatively inexpensive plastics material, to provide a body fluid separation means for one use only and then to be disposed of.

According to a fourth aspect of the invention, a method of separating body fluid into selective component parts comprises applying a sample of body fluid to one side of a filter, applying vacuum to the opposite side of the filter to draw body fluid through the filter and to leave the specified component trapped on the filter, and releasing the specified component from the filter either in situ or following removal of the filter.

Thus, with particular reference to the separating of the DNA content of blood, and for which the invention in its second aspect is particularly suited, a whole blood sample is applied to one side of a filter, vacuum is applied to the opposite side of the filter to draw the whole blood sample therethrough and separate the plasma and red cell content of the blood from the leukocyte cell content, leaving the leukocyte content trapped in the filter, followed by the application of water or, preferably, isotonic saline, to the same side of the filter to be drawn therethrough by the vacuum applied to the opposite side of the filter to lyse the leukocyte cells trapped in the filter. As an alternative to the application of water/isotonic saline, a chemical lysing agent or compatible cell detergent can be used to separate the plasma and red cell content of the blood from the leukocyte cell content, and to leave the leukocyte content trapped in the filter. Following lysing the, such as, removable end cap on the chamber now containing what is waste material can be removed and discarded, the chamber inverted and isotonic saline applied to the opposite side of the filter to wash out the cell contents of the leukocyte cells from the filter into an appropriate receptacle from where the DNA content is removed. The suitable receptacle may be the removable end cap on the other end of the chamber. Alternatively, following removal of the end cap containing waste material, it can be replaced by the end cap from the opposite side of the chamber, and isotonic saline can be applied to the same side of the filter to wash out the cell contents of the leukocyte cells into the clean end cap, from where the DNA content can be removed. As a still further alternative, it is possible for certain tests to leave the leukocyte content trapped in the filter and to serve as a test base for a variety of medical tests.

In the circumstance where it is the removal of leukocyte cells, it is preferred that the commercially available filter known in trade as Pall LK4 is used. It is also preferred that the end cap to receive the cell contents is provided with a suitable membrane to isolate the DNA content of the cells from other cell debris washed from the filter to provide a clean DNA sample able to be liberated from the membrane utilising conventional transfer techniques. The invention, in its application to DNA harvesting and leukocyte testing, by its equipment and its method avoids completely the need for any preparation of a blood sample, and allows the separation, collection, and gathering of the DNA content in exceedingly simple and efficient manner.

Whole blood may simply be applied to the filter through the open end of the chamber, without pre-preparation, and vacuum applied to the opposite side such as by a relatively simple laboratory vacuum pump, or by, for example, a standard medical syringe. This causes red cells and plasma to be drawn through the filter and collected in a removable end cap, leaving leukocytes trapped in the filter. With continued application of vacuum, water, isotonic saline, or a chemical lysing agent, or a compatible cell detergent is then applied to and drawn through the filter, causing chemical lysing, or lysing of the leukocytes by osmotic shock.

Once the cell contents have been collected, the DNA component can then be gathered by conventional techniques.

In other spheres of testing such as, for example, foetal testing, sperm counting, bone marrow testing, urine, and saliva testing, it is desirable to provide multiple samples, and for which the invention in its third aspect is particularly suited. Here, a sample is applied to each of the number of filters overlying a respective waste collection chamber on the second plate following which the first plate is applied to the second plate to trap the filters and the assembly of first and second plates applied to the third vacuum forming plate.

Thus, in the case of the screening and isolation of foetal trophoblasts (immature blood cells) from maternal blood a filter that allows the passage of maternal blood cells and which entraps foetal blood cells is employed, for example, a Pall J100 or similar membrane, with the gel-coated side positioned to receive the blood sample. The filter is further coated to render it non-stick, as is the sample collection chamber. A whole blood sample taken from a mother need not be the subject of any prior preparation and can be applied to each of the number of filters. With vacuum applied via the vacuum chamber to the waste collection chamber maternal blood cells of the blood are drawn through the filter and collected in the waste collection chamber, whilst foetal blood cells are left entrapped in the filter. The second and third plates are removed and the waste material in the waste collection chambers discarded, and the first plate inverted. Here again, it is preferred that the foetal cells are released from the filter into the collection chambers from where they can be removed for test. It is, however, possible that the foetal filters can be stripped of debris to leave the cells trapped in the filter and tests effected on the cells whilst on the filter.

In its preferred form, a procedure for isolating and screening foetal trophoblasts comprises isolating foetal blood cells from a maternal blood sample using a specially prepared membrane which allows the maternal blood cells to pass through the membrane leaving the foetal blood cells trapped within the filter, the foetal blood cells then being lysed and a chemical and specific antibody marker compatible with specific chromosomes added, the marker having the ability to fluoresce under shortwave ultra violet light to signal an abnormality in the foetal cells. Thus, as in the example of Downs Syndrome, chromosome 21 will be shown to be present in triplicate, instead of in duplicate. The chromosome 21 will appear on the screen under UV light as three fluorescent dots.

It is envisaged that this non-invasive screen could be carried out from 10 weeks gestation. The technique can be used for any other genetically carried syndromes i.e. Huntingdons chorea, cystic fibrosis, and spina bifida.

BRIEF DESCRIPTION OF THE DRAWINGS

The invention will now be further described, by way of example only, with reference to the accompanying drawings, in which:

FIG. 2 is an exploded perspective view of a second embodiment of the invention, particularly for multi-sample body fluid testing; and FIG. 3 is a section on the line III—III of FIG. 2, in its assembled condition.

DESCRIPTION

Figure 1:
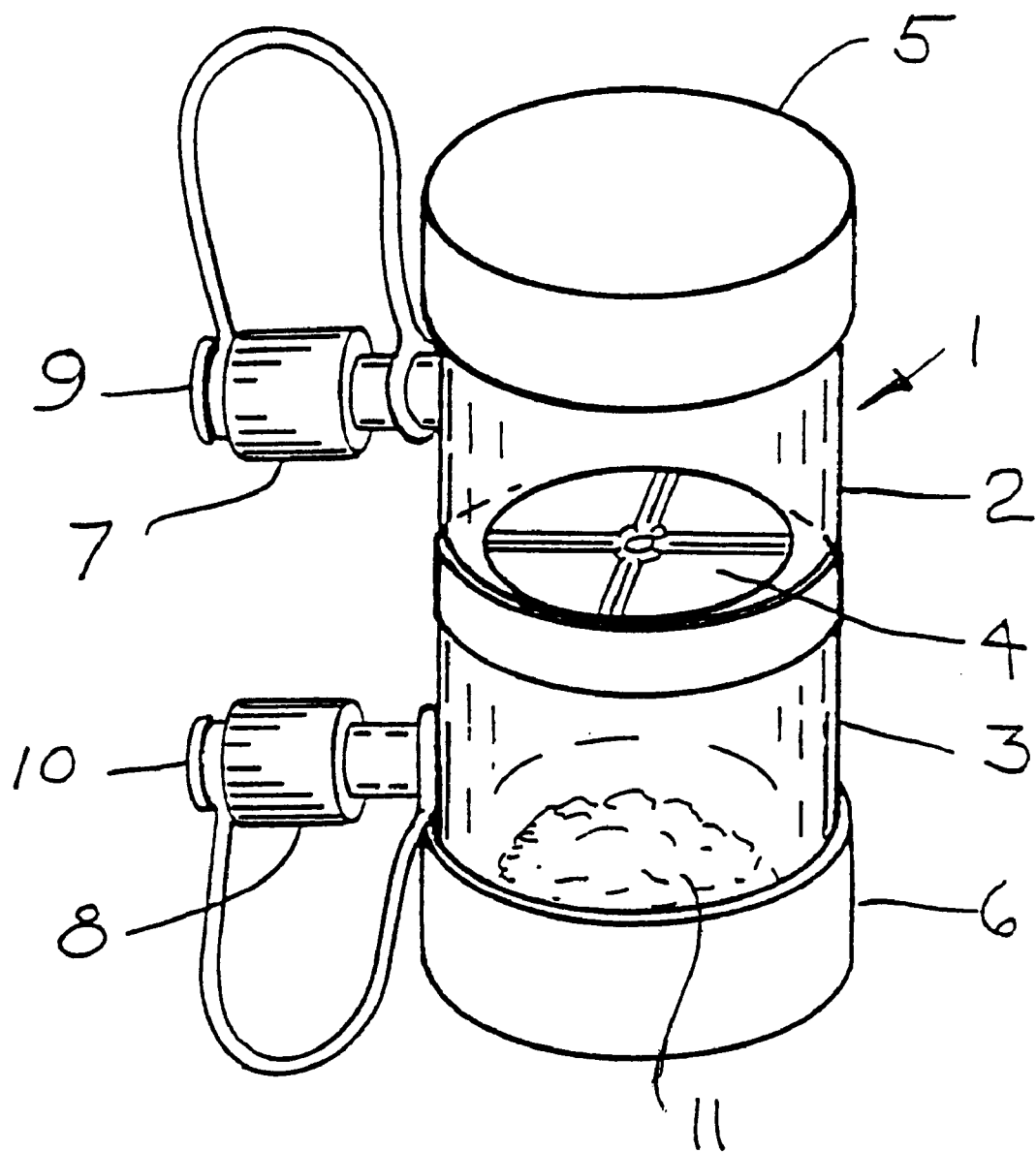
FIG. 1 is a perspective view of a first embodiment of the invention, particularly for DNA harvesting.

In FIG. 1 a body fluid separation means particularly suited to DNA harvesting is formed by a chamber 1 having upper and lower sectors 2, 3, and a centrally disposed filter 4. Each of the upper and lower sectors 2, 3, is provided with a removable end cap 5, 6, respectively, each end cap being in sealing engagement with the respective end of the chamber sector. Each sector has a connection 7, 8 closed by a respective plug 9, 10 to enable either or both of the chamber sectors 2, 3, to be connected to a source of vacuum.

At the outset, the end cap 5 is removed and a whole blood sample introduced into the chamber and on to the filter 4, such as by way of a conventional syringe. The end cap 5 is replaced, the plug 10 removed from the connection 8 on the lower sector 3 of the chamber, and the connection 8 connected to a source of vacuum, which again may be by way of a conventional syringe, the presence of vacuum below the filter causing blood to be drawn through the filter. The filter is specifically chosen to enable the leukocyte content of the blood to be trapped on it, the plasma and red cell content of the blood drawn through the filter being deposited in the end cap 6. Following this, the end cap 5 is removed and water, isotonic saline, an appropriate chemical lysing agent or a compatible cell detergent is applied to the filter and drawn through the filter by the vacuum existing below it and the end cap 5 then replaced. The cap 6 is removed and the waste material contained in it discarded, following which the container can be inverted, the plug 10 is replaced on the connection 8, the plug 9 removed and the connection 7 connected to vacuum. With water or isotonic saline then applied to the opposite side of the filter, the cell contents of the leukocyte cells are washed out to be gathered in the cap 5. Following this the cap 5 can be removed to allow the harvesting of DNA content. As an alternative to this, and following the removal of the end cap 6, the end cap 5 can be applied to the container in place of the end cap 6, water, isotonic saline, a chemical lysing agent, or compatible cell detergent applied to the same side of the filter to wash out the cell content of the leukocyte cells into the end cap 5 by the continued application of vacuum through the connection 8.

Whichever of the caps 5, 6, is employed to gather the cell contents of the leukocyte cells, it is most desirable that a filter membrane 11 is provided to isolate the DNA content of the cells from any other cell debris washed from the filter, the membrane being readily removable from the end cap for the subsequent stripping of the isolated DNA content.

In FIGS. 2 and 3 body fluid separation means for the simultaneous treatment of a number of samples is shown.

Although the embodiment illustrates the treatment of six samples simultaneously, it will be appreciated that any number of samples can be dealt with. In this embodiment, there is provided a first plate 12 formed with six collection chambers 13, and a second plate 14 formed with six cooperating waste receiving chambers 15. Each waste receiving chamber 15 has a connection port 16 to connect each waste receiving chamber to a vacuum chamber 17 formed in a third plate 18, the third plate 18 having a connection 19 to a source of vacuum (not shown). Contained in the vacuum chamber 17 is a membrane 20. Thus with the second plate 14 located on the third plate 18, and with individual filters 21 positioned over each waste receiving chamber, a sample of body fluid is applied to each filter, and the first plate 12 positioned on the second plate to provide the assembly as is indicated by FIG. 3. With vacuum applied through 19 to the chamber 17 a vacuum is applied through each port 16 to the waste collection chamber, to cause the plasma/fluid content of the sample on the filter to be drawn through the filter into the waste receiving chamber 15, from where it passes through the port 16 for collection on the membrane 20. The third plate 18 is removed and the waste material on the membrane 20 discarded, the first and second plates inverted and the second plate removed to allow access to the filters and to enable the cells or other body fluid components trapped on the filter to be washed into the sample collection chambers 13.

Such an apparatus as is illustrated by FIGS. 2 and 3 is eminently suited to, such as for example, the screening and isolation of foetal trophoblasts from maternal blood, an appropriate membrane/filter being employed that is gel coated, the blood sample being applied to the gel-coated side, and the membrane/filter together with each collection chamber being further treated to render it non-stick, it being known that foetal trophoblasts readily adhere to other substances. Once the foetal trophoblasts have been isolated, a genetic probe can be applied to the cells which probe is specific to a given chromosome, for example chromosome 21 which, if it appears in triplicate instead of duplicate, confirms a diagnosis of Down's syndrome. The technique of fluorescent in situ hybridisation, either interphase or metaphase, probes can be used to identify all known genetic disorders. In situ fluorescence can be visualised with a simple microscope or ultra-violet reader, when the probe specific to the chromosome to be examined would be seen as fluorescent dots (e.g. two dots—Down's negative and three dots—Down's positive).

What is claimed is:

1. A body fluid separation means comprising at least one first chamber (2), a cooperating filter(s) (4) extending across the or each first chamber and at least one second chamber (3) respectively to cooperate with the at least one first chamber characterized in that one or both of said first and second chambers (2, 3) has a connection (7, 8) to vacuum, positioned to one or both sides of the filter (4) and there being a removable closure means in the form of end caps (5, 6) at the end of each chamber, wherein the body fluid separation means is disposable, and wherein the end caps (5, 6) are interchangeable.

2. A body fluid separation means as in claim 1, characterised in that the filter (4) is pre-treated to suit the use to which the body fluid separation means is to be put.

3. A body fluid separation means as in claim 1, characterised in that a leukocyte trapping membrane filter is provided.

4. A body fluid separation means as in claim 2, characterised in that for the separation of cells a replaceable filter (4) is provided with characteristics able to permit the passage of blood or plasma and entrap the cells required for test.

5. A body fluid separation means as in any of claims 1, 2 3 or 4, characterised in that the material of the chamber(s) (2, 3) and the cap(s) (5, 6) is such that they are sterilisable.

6. A method of using a body fluid separation means to separate body fluid into selective component parts, wherein the body fluid separation means includes at least one first chamber (2), a cooperating filter(s) (4) extending across the or each first chamber and at least one second chamber (3) respectively to cooperate with the at least one first chamber characterized in that one or both of said first and second chambers (2, 3) has a connection (7, 8) to vacuum, positioned to one or both sides of the filter (4) and there being a removable closure means in the form of end caps (5, 6) at the end of each chamber, wherein the body fluid separation means is disposable, and wherein the end caps (5, 6) are interchangeable, said method characterised by applying a sample of body fluid to one side of the filter (4) in the first chamber (2) applying, vacuum to the opposite side of the filter to draw body fluid through the filter and into the removable closure means (6) and leave the specified component trapped on the filter, and releasing the specified component from the filter into a further removable closure means (5), following removal of the removable closure means (6), and either the inversion of said body fluid separation means comprising the filter (4), or the relocation of the further removable means (5) to the end of said second chamber (3).

* * * * *